United States Patent
Clarke

(10) Patent No.: US 6,208,887 B1
(45) Date of Patent: Mar. 27, 2001

(54) CATHETER-DELIVERED LOW RESOLUTION RAMAN SCATTERING ANALYZING SYSTEM FOR DETECTING LESIONS

(76) Inventor: Richard H. Clarke, 64 Pinckney St., Boston, MA (US) 02114

( * ) Notice: Subject to any disclaimer, the term of this patent is extended or adjusted under 35 U.S.C. 154(b) by 0 days.

(21) Appl. No.: 09/339,524

(22) Filed: Jun. 24, 1999

(51) Int. Cl.[7] ...................................................... A61B 5/00
(52) U.S. Cl. ........................ 600/476; 600/478; 600/342; 606/15; 356/301
(58) Field of Search ................................... 600/476, 478, 600/342; 606/2, 3, 10, 15; 356/301

(56) References Cited

U.S. PATENT DOCUMENTS

| | | | |
|---|---|---|---|
| 4,913,142 | * 4/1990 | Kittrell et al. | 606/7 |
| 5,139,334 | 8/1992 | Clarke | 356/301 |
| 5,199,431 | * 4/1993 | Kittrell et al. | 600/476 |
| 5,280,788 | * 1/1994 | Janes et al. | 600/476 |
| 5,439,000 | * 8/1995 | Gunderson et al. | 600/476 |
| 5,452,723 | 9/1995 | Wu et al. | 128/664 |
| 5,455,673 | 10/1995 | Alsmeyer et al. | 356/301 |
| 5,615,673 | 4/1997 | Berger et al. | 128/633 |
| 5,773,835 | 6/1998 | Sinofsky | 250/462.1 |
| 5,842,995 | * 12/1998 | Mahadevan-Jansen et al. | 600/476 |
| 5,902,246 | * 5/1999 | McHenry et al. | 600/476 |
| 5,902,247 | * 5/1999 | Coe et al. | 600/476 |
| 5,951,482 | * 9/1999 | Winston et al. | 600/476 |
| 5,993,378 | * 11/1999 | Lemelson | 600/109 |

OTHER PUBLICATIONS

Salenius, J. P. et al, "Biochemical Composition of Human Peripheral Arteries Examined With Near–Infrared Raman Spectroscopy", J. of Vascular Surgery, V. 27, N. 4, p. 710, 1998.*

Brennan, James F. et al, "Histochemical Analysis of Human Coronary Artery Using Near–Infrared Raman Spectroscopy", Proc. of SPIE, Intl. Soc. for Optical Engr., V. 2324, p. 98, 1995.*

Riva, R.P. et al, "Near Infrared Fouier Transform Raman Spectroscopy of Human Artery", Spectrochimica Acta, Part A (Mol. Spec.), vol. 47A, No. 3–4, p. 509–12, 1991.*

"Near–Infrared Raman Spectrometer Systems for Human Tissue Studies", James F. Brennen III, et al., Applied Spectroscopy, vol. 51, No. 2, 1997, pp. 201–208.

* cited by examiner

Primary Examiner—John A. Jeffery
(74) Attorney, Agent, or Firm—Thomas J. Engellenner; Nutter, McClennen & Fish, LLP

(57) ABSTRACT

The present invention provides low resolution Raman spectroscopic systems and methods for in-vivo detection and analysis of a lesion in a lumen of a subject. The system uses a multi-mode laser attached to a catheter in making in-vivo Raman spectroscopic measurements of the lumen. The system includes a light collector and/or a light dispersion element as well as a detector to measure spectral patterns that indicate the presence of the lesion. Based on the spectral response of the lumen, the presence (or absence) of a lesion can be determined. In addition, the components of the lesion can also be identified based on the unique Raman spectrum associated with each component.

21 Claims, 4 Drawing Sheets

CATHETER-DELIVERED LOW RESOLUTION RAMAN SCATTERING ANALYZING SYSTEM FOR DETECTING LESIONS

BACKGROUND OF THE INVENTION

The technical field of this invention is low resolution Raman spectroscopy for invivo analysis of a sample, for example, analysis of blood vessels for atherosclerotic plaques using low resolution Raman spectroscopy.

It is well known that deposits of plaque on cardiovascular tissues, such as on the interior walls of arteries, can severely restrict or completely block the flow of blood. Plaques typically exists in two forms, namely, as calcified plaques or as fibrous plaques. Calcified plaques are more rigid and more difficult to remove than fibrous plaques. Previous studies suggest that plaque composition rather than the actual size or volume of the plaque determine acceleration of clinical symptoms (Loree et al. (1994) *Artheroscler. Thromb.* 14, 230–234). Thus, methods for detecting deposits of calcified plaque or fibrous plaque on blood vessels, and determining their composition, have substantial utility in the diagnosis and treatment of atherosclerosis and related cardiovascular ailments.

A variety of spectroscopic methods have been used to characterize arterial disease in situ (See e.g., Clarke et al. (1988) *Lasers Surg. Med.* 8: 45–59; Deckelbaum et al. (1995) *Lasers Surg. Med.* 16: 226–234; Yan et al. (1995) *Lasers Surg. Med* 16: 164–178; Manoharan et al. (1993) *Artheroschlerosis* 103: 181–193 and Baraga et al. (1992) *Proc. Natl. Acad. Sci.* 89: 3473–3477). By delivering excitation light and collecting emitted light through flexible optical fibers, fluorescence spectra from a coronary artery can be collected and used to differentiate normal tissue from abnormal tissue (Bartorelli et al. (1991) *J. Am. Coll. Cardiol.* 17:160B–168B and Richards-Kortrum et al. (1989) *Am. Heart J.* 118: 381–391). However, due to the limited difference in fluorescence spectra of chemical compounds, these spectra typically provide insufficient chemical composition information.

In contrast, Raman spectroscopic methods provide more detailed spectra capable of providing greater compositional information and an ability to differentiate normal from abnormal tissue. For example, Clarke et al. discuss using visible Raman spectroscopy to analyze the surface of diseased and healthy tissue sites on post-mortem specimens of calcified aortic valves and coronary artery segments (see Clarke et al. (1988) *Lasers in Surgery and Medicine,* 8, 45–49).

In Raman Spectroscopy of Atherosclerotic Plaque: Implications for Laser Angioplasty," Radiology, 177, 262 (1990), Redd et al. also disclose using visible Raman spectroscopy to analyze human cadaveric aorta, percutaneous peripheral atherectomy, and surgical endarterectomy samples and conclude that Raman spectroscopy allows fatty plaque to be distinguished from a normal artery.

Recently, Brennen et al. described using IR Raman spectroscopy to analyze the chemical composition of human coronary artery from homogenized coronary artery samples (Brennen et al. (1997) *Applied Spec.* 52; 201–20).

However, prior approaches to the use of Raman spectroscopy have been largely, if not entirely, limited to the characterization ex-vivo of specimens removed from the subject by excision or extraction. The limitation of Raman spectroscopy to post-surgical (or post-mortem) analysis was due to the large optical systems needed to obtain a high resolution spectrum.

Another drawback to IR Raman spectroscopy has been its expense of operation. A significant component of that expense is the laser system required to produce quality, high-resolution spectra. Even using a laser diode as the scattering source, the laser remains one of the major expenses in developing cost-effective Raman systems.

Thus, there exists a need for a low cost, simple Raman spectroscopic system for in-vivo analysis of a sample. Moreover, there exists a specific need for systems for analyzing the chemical components of atherosclerotic plaques in-vivo.

SUMMARY OF THE INVENTION

The present invention is directed to low resolution Raman spectroscopic systems for in-vivo detection and analysis of a lesion in a lumen of a subject, for example, analysis of blood vessels for atherosclerotic plaques. In one aspect of the invention, a multi-mode laser is employed in making in-vivo Raman spectroscopic measurements of the lumen. The system can also include a light collector and/or a light dispersion element as well as a detector to measure spectral patterns that indicate the presence of the lesion. Based on the spectral response of a target (e.g. a lumen), the presence (or absence) of a lesion can be determined. Furthermore, the components of the lesion can also be identified based on the unique Raman spectrum associated with each component.

Accordingly, in one aspect, the present invention provides a system for detecting the presence of a lesion in the lumen of a subject using low resolution Raman spectroscopy. The system can include a catheter comprising an excitation fiber through which multi-mode radiation can propagate to irradiate a target region of a lumen, a multi-mode laser for irradiating the target region to produce a Raman spectrum consisting of scattered electromagnetic radiation, a low resolution dispersion element positioned to receive and separate the scattered radiation into different wavelength components, a detection array, optically aligned with the dispersion element for detecting at least some of the wavelength components of the scattered light, and a processor for processing data from the detector array.

In use, the multi-mode laser irradiates the target to produce a Raman spectrum. The Raman spectrum is composed of scattered electromagnetic radiation characterized by a particular distribution of wavelengths. The Raman spectrum is a result of the scattering of the laser radiation as it interacts with the target.

The collector element collects the radiation scattered from the target. The collection element can be an optical fiber. The collection fiber can have a first end positioned for collecting scattered radiation, and a second end positioned in selected proximity to the dispersion element. One or more filters can also be employed in the systems of the present invention to reduce or attenuate optical "noise". For example, a notch filter can be coupled to the first end of the collection fiber for filtering the excitation source background.

The dispersion element distributes the scattered radiation into different wavelength components. The detection array detects the scattered radiation in different wavelength ranges, and a processor processes the detected array data to detect the presence and/or the components of the lesion.

The system further includes a catheter comprising a light directing element, where the excitation fiber has a first end coupled to the multi-mode laser, and a second end coupled to the light directing element to direct the laser radiation to the lesion. The excitation fiber transmits the laser radiation from the multi-mode laser to the light directing element which directs the laser radiation to the lesion in the lumen.

In some features of the present invention, the resolution of the apparatus is determined in part by the full-width at half-maximum (FWHM) of the spectral distribution of the multi-mode laser, and, in part, by the dispersion element. In one embodiment, the apparatus preferably has a resolution of between 10 cm and 100 cm$^{-1}$ and most preferably between 30 cm and 50 cm.

According to some features of the present invention, the multi-mode laser element produces laser radiation having a wavelength between about 700 nanometers (nm) and about 2.4 micrometers ($\mu$M), more preferably between 700 nm and about 1.1 $\mu$M. Preferably, the multi-mode laser produces radiation having a line width of at least 2 nm. The multi-mode laser preferably has a power between about 50 milliwatts (mW) and about 1000 mW, and more preferably, greater than about 150 mW in some applications. One example of a multi-mode laser element for use with the present invention is a 785 nm GaAs laser diode. This GaAs multi-mode laser has a spectral distribution FWHM of approximately 30 cm.

According to other features of the present invention, the processor can include a chemometric element for applying partial least square analysis to extract additional information from the Raman spectrum. The dispersion element can be a low resolution spectrometer. The low resolution spectrometer can be a monochromator. The detection array can be a diode array detector. Alternatively, the detection array can be a non-cooled charged coupled device detector. The collection fiber can include a fiberoptic immersion probe.

In another aspect, the invention features a method for detecting the presence of a lesion in a lumen of a subject using low resolution Raman spectroscopy. The method includes providing a catheter comprising an excitation fiber through which multi-mode radiation can propagate, the excitation fiber having a light directing element and having a first end coupled to a multi-mode laser, and a second end positioned to direct radiation to a site within a lumen, inserting the catheter into the lumen,
activating the multi-mode laser to irradiate the lumen to produce a Raman spectrum consisting of scattered electromagnetic radiation, collecting a portion of the scattered radiation, separating the collected radiation into different wavelength components using a low resolution dispersion element, detecting at least some of the wavelength components of the scattered light using a detection array, and processing the data from the detection array to detect the presence of a lesion.

The method can also include the further step of identifying the components of the lesion. Components of the lesion can be identified based on the unique Raman spectra associated with each component.

The invention is particularly well-suited for the detection of atherosclerotic plaque lesions in a blood vessel of the subject. In one embodiment, various components of the atherosclerotic plaque can be detected and/or quantitatively analyzed. Preferably, the components are selected from the group consisting of cholesterol esters, calcium salts, free cholesterol, phospholipids and triglycerides.

This invention is particularly useful in that it can provide a quick and reliable invivo method for detecting the presence of a lesion in a lumen. The present invention also permits a chemical analysis of the components of the lesion in a single step procedure, without resorting to elaborate multi-step methods.

The invention will next be described in connection with an illustrated embodiment. However, it should be clear that various changes, additions and subtractions can be made without departing from the spirit or the scope of the invention.

BRIEF DESCRIPTION OF THE DRAWINGS

The invention will be more fully understood from the following detailed description taken in conjunction with the accompanying drawings, in which.

DETAILED DESCRIPTION

Figure 1:
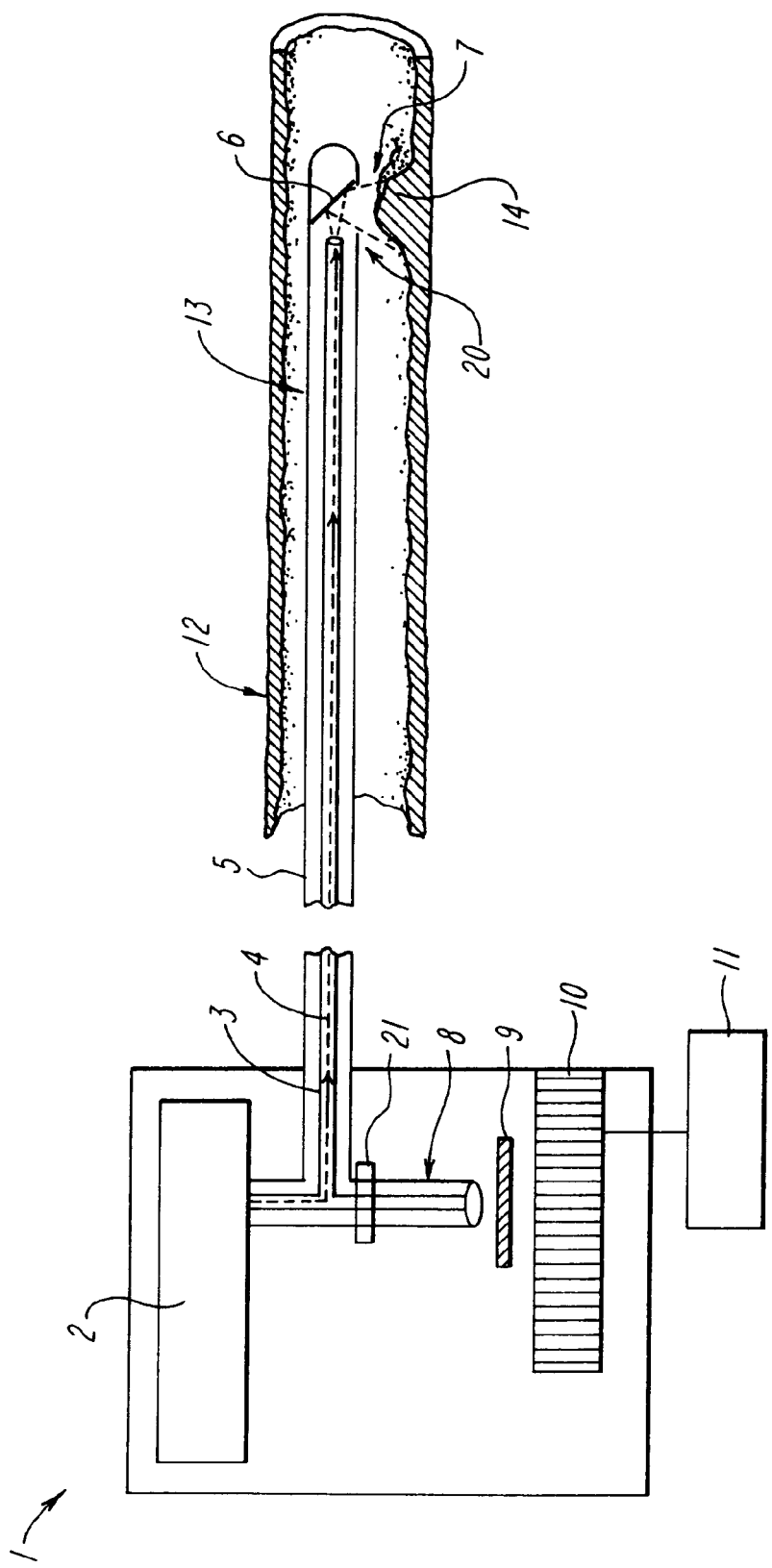
FIG. 1 is a block diagram of a sensor system of the invention.

FIG. 1 is a block diagram of a sensor system 1 that is particularly well-suited for in-vivo detection and analysis of a subject. System 1 includes a multi-mode laser source 2, connected to an excitation fiber 3, that carries multi-mode laser/radiation 4, via a catheter 5, to a light directing element 6, which directs the laser/radiation in a sideways direction producing directed radiation 7. The directed radiation 7, exits the catheter via an orifice 20, and irradiates a lesion 14, within a lumen 13 with a vessel wall 12. The lesion produces Raman scattered radiation that is collected by a collection fiber bundle 8, through which the radiation travels to a low resolution dispersion element 9, that serves to disperse the scattered light into its different wavelength components, that are detected by a detection array 10, and analyzed by a microprocessor 11.

The excitation fiber 3, is connected at its proximal end to the multi-mode laser 2 and has a distal end adjacent to a light directing element 6. Multi-mode laser radiation 4, is carried through the excitation fiber 3, exiting at the distal end towards the light directing element 6, which directs the multi-mode laser radiation in a sideways direction. The light directing element can be a material that is reflective, refractive or diffusive. The directed radiation 7, exits the catheter through an orifice 20, and irradiates a lesion 14.

Raman scattered radiation from the lesion 14, is collected by an optical waveguide and is transmitted back into the catheter. The scattered radiation is collected by the fiber bundle 8, which may optionally have a notched filter 21. The scattered radiation is dispersed into various components by the dispersion element, and detected by the detective array 10.

A Powertechnology multi-mode laser HPM 500 (785-1000) FIX12, (Powertechnology, LittleRock, Ark.) can be used as a multi-mode laser. The dispersed scattered light is detected by photodetector array 10 that, in this case, consists of a photodiode array or a charged-coupled device (CCD) array.

The resolving power of the dispersion device 9, determines the position of specific wavelengths in the diode array in such a way that the signal from a particular diode in the array will typically correspond to the same (or a similar) narrow range of wavelengths. This combination of the low-resolution dispersion device 9, and the diode array photodetector 10, thus form a Raman spectrometer. The microprocessor 11, selects a particular diode (or diodes) of the array 10, according to the property to be measured. The integrated signals lying in the two ranges can be arithmetically divided to form intensity ratios. The microprocessor 11, compares these ratios with known values or a correlating function to obtain an estimate of the chemical constituent or property of interest.

Advances in the field of solid state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 milliwatts (mw) and 1000 mw) than is available with a traditional single mode laser (<150 mw). The higher power of a multi-mode laser increases the amount of scattered radiation available to the spectrometer system. The sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to the detector array. Thus, the combination of a low cost, high energy multi-mode laser and a low loss dispersion element provides an inexpensive LRRS system that provides a high intensity signal.

In a typical LRRS application the need for feature separation is much like that encountered in mid-IR spectroscopy. The use of multi-mode lasers causes a degradation in the resolution of the spectrometer. The resolution of the LRRS system decreases primarily because the width of the laser line used to excite the sample is much larger with multi-mode lasers than it is with a single mode laser. A multi-mode laser has a linewidth of 2–3 nanometer. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid state laser sources are both sufficient for the task and cost effective, and high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multimode laser, the width of the slits can be increased with negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by notch filters capable of removing the excitation source background.

U.S. Pat. No. 5,139,334 issued to Clarke, and incorporated herein by reference, teaches a low resolution Raman spectral analysis system for determining properties related to hydrocarbon content of fluids. The system utilizes a Raman spectroscopic measurement of the hydrocarbon bands and relates specific band patterns to the property of interest.

The present invention provides a similar system for detecting in-vivo samples based on a change in the Raman scattered radiation produced in the presence or absence of a lesion in a lumen of a subject. The invention also provides a system for identifying the components of the lesion based on the difference in the Raman spectrum patterns associated with each component, discussed in more detail below.

Figure 2:
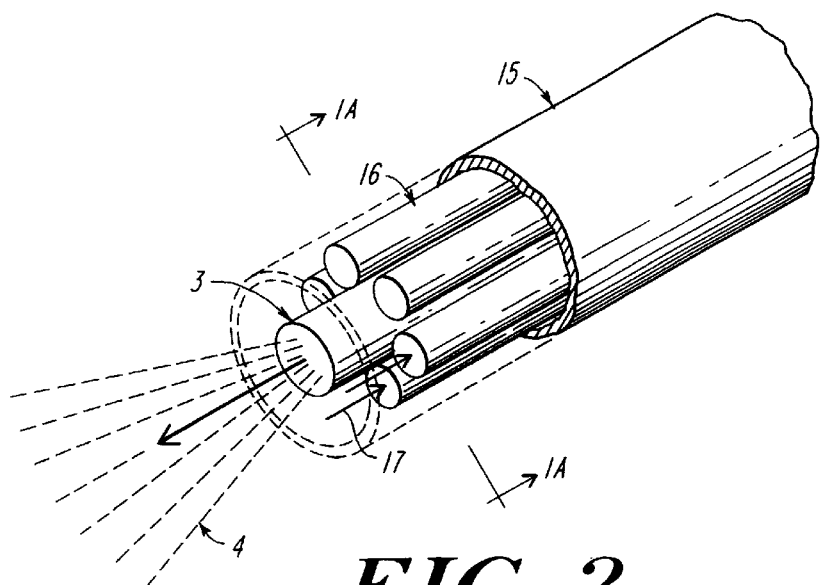
FIG. 2 is a schematic, partially cut away, perspective view of an apparatus for spectral analysis.

FIG. 2 shows one embodiment of the invention. FIG. 2 is an apparatus for spectroscopic analysis that includes a casing or sheath 15, an excitation fiber 3, through which radiation can be transmitted and emitted as a conical pattern of excitation radiation 4. The apparatus further includes a number of fibers 16, which receive Raman scattered radiation 17, from the surrounding lumen. Although illustrated as optical fibers, it should be apparent that means can be any light waveguide or assembly of optical elements known in the art, for collection of radiation form the lumen.

Figure 2A:
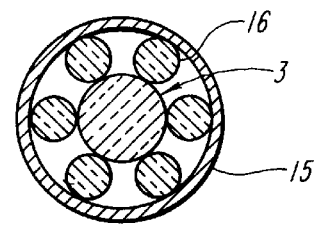
FIG. 2A is a cross sectional view of the apparatus of FIG. 2 taken along section line A—A.

FIG. 2A is a cross sectional view of the apparatus shown in FIG. 2, illustrating the relative positions of the excitation fiber 3, and the collections fibers 16, as well as the protective sheath 15.

Figure 3:
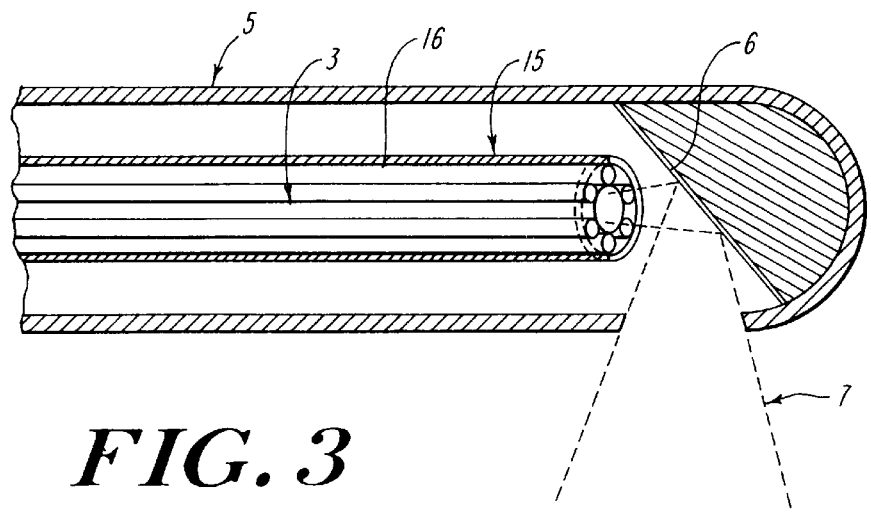
FIG. 3 is another partially, cross sectional view of another apparatus for spectroscopic analysis according to the invention.

FIG. 3 is an apparatus for spectroscopic analysis which includes a catheter 5, that has an excitation fiber 3, and collection fibers 16, surrounded by a sheath 15. The catheter 5, also includes a light directing element 6, which directs multi-mode laser radiation in a sideways direction to produce directed light 7, used to irradiate a lesion in the lumen.

Figure 4:
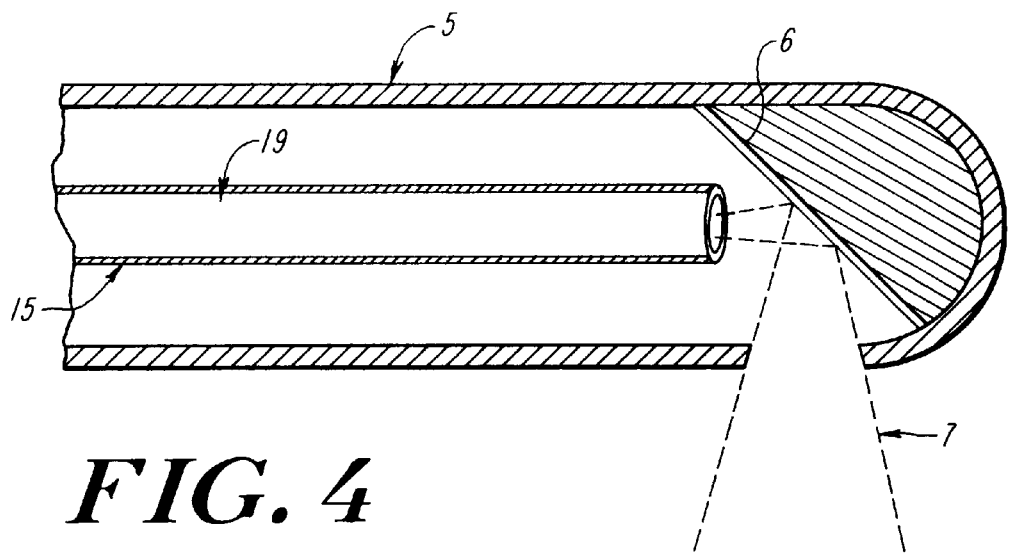
FIG. 4 is another partially, cross sectional view of another apparatus for spectroscopic analysis according to the invention.

FIG. 4 is an alternative apparatus which includes a single fiber 19, surrounded by a sheath 15. The fiber serves as both the excitation fiber and the collection fiber. The fiber directs multi-mode laser radiation to the a light directing element 6, which directs the laser radiation in a sideways direction to produce directed light 7, used to irradiate a lesion in the lumen.

The invention also provides a method of detecting the presence of a lesion in the lumen of a subject. The subject can be selected from the group consisting mammals, birds, reptiles or amphibians. Preferably, the subject is a mammal, most preferably a human.

It is known that normal and diseased tissue of a given type, exhibit distinct spectroscopic features. These characteristics are sufficiently different to enable rapid diagnosis, for example, when an atherosclerotic plaque-arterial wall boundary is encountered. Accordingly, a simple spectral analysis will identify the presence of an atherosclerotic plaque in the artery.

The invention also provides a method of determining whether an atherosclerotic plaque is fibrous or calcified based on the difference in Raman spectrum obtained from a fibrous atherosclerotic plaque and a calcified plaque. Therefore, by comparing the IR Raman spectrum from a tissue sample, for example, arterial wall tissue, whose condition is known with a standard IR spectrum from a tissue obtained from a calcified atherosclerotic tissue, a fibrous atherosclerotic tissue, or from normal tissue for the same type of tissue being tested (e.g., human aortic tissue compared to human aortic tissue standards), it is possible to determine whether the tissue is calcified, fibrous or normal.

These types of comparisons can be made in a number of ways, for example, by comparing the characteristic Raman lines in a spectrum for a tissue sample, with the number of characteristic lines with the standard spectra. Another example includes, comparing the ratio of intensities of two characteristic Raman lines which are common in the spectra for the tissue in its calcified, fibrous or normal state with the respective ratios for calcified atherosclerotic, fibrous or normal tissue for the same type of tissue being tested. The correlation of a previously stored spectrum may be used to determine whether the spectrum of the scattered Raman radiation is similar to the spectrum of an atherosclerotic plaque, or of an arterial wall, and the resulting comparison may be displayed in a numerical form by the microprocessor.

Standards can be established for example, by obtaining Raman spectra from tissue samples containing atherosclerotic plaques, fibrous plaques and normal arterial walls excised from human cadavers. The separate Raman spectra for each tissue sample can be stored in microprocessor to be used as standards. Using the method of the invention, subsequent in-vivo analysis of the human lumen will then generate Raman spectra that can be compared against the standard spectra obtained from cadaveric tissue. This would not only identify the presence of a plaque in the lumen, but would also identify whether the plaque was calcified or fibrous. Determination of whether a plaque is calcified or fibrous aids in determining the appropriate course of action required to treat the plaque.

The invention also provides a method of determining the components of an atherosclerotic plaque. The components can be determined, for example, by establishing an average weight of each component from homogenized human cadaveric arteries and analyzing the resulting Raman spectra. The data can be processed to calculate the average weights of free cholesterol, cholesterol esters, total cholesterol, phospholipids and calcium salt in the volume of tissue sampled. The Raman spectral features can be modeled as a combination of individual chemical components of free cholesterol, cholesterol esters, calcium salts, total cholesterol, phospholipids and delipilized arterial tissue described by Press et al. (1992), Numerical Recipes, Cambridge university press, 15: 671–680. The relative weights of arterial chemical components can be used to diagnose normal tissue, fibrous atherosclerotic plaques and calcified atherosclerotic plaques using an algorithm with the discriminant analysis technique of logistic regression as described by Römer et al. (1998) *Circulation*, 97, 878–885. Using the relative weight of the components, it is possible to calculate the probability that the artery is normal, contains a fibrous atherosclerotic plaque, or contains an atherosclerotic calcified plaque by a comparison of in-vivo Raman spectra from a lesion, with the calculated weights of components.

One skilled in the art can appreciate that the present invention may also be useful in other fields, which include but are not limited to, oncology, urology, gastroenterology, neurosurgery, general surgery and obstetrics/gynecology.

As an indicator of in-vivo analysis using low resonance Raman spectroscopy, the following figures indicate the changes envisioned between a normal artery, an artery with a fibrous plaque and an artery with a calcified plague.

Figure 5A:
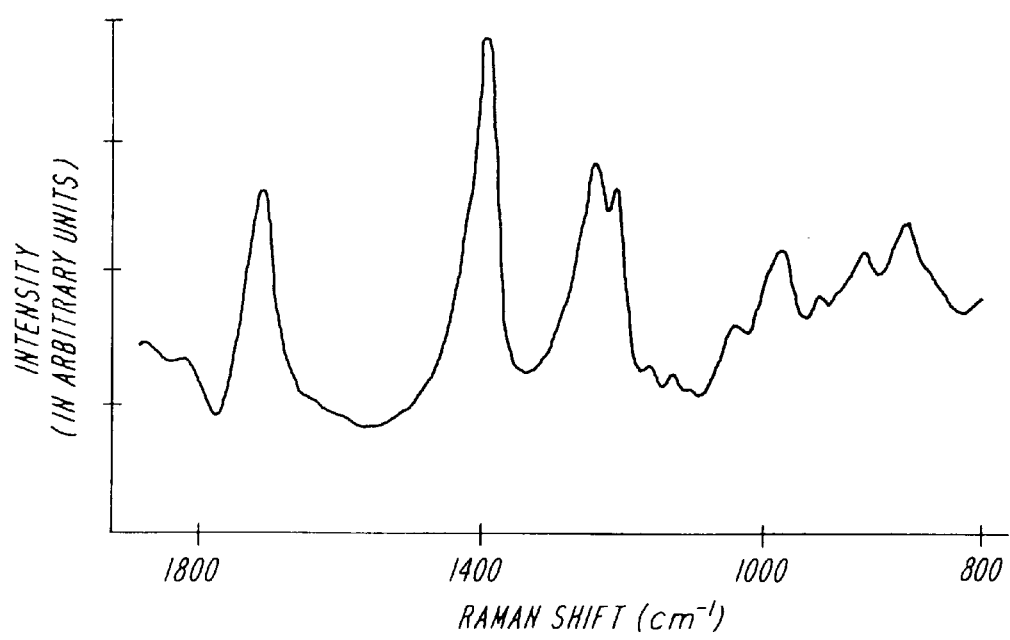
FIG. 5A is a graph of intensity in arbitrary units versus Raman shift wavelength for a normal arterial lumen.

FIG. 5A is a graph of intensity in arbitrary units versus Raman shift wavelength for a normal arterial lumen. The graph shows triglyceride and protein features at approximately 1650, 1250 and 1450 $cm^{-1}$ Raman shifts. This is typical of arterial walls which are composed of protein fibers and smooth muscle cells.

Figure 5B:
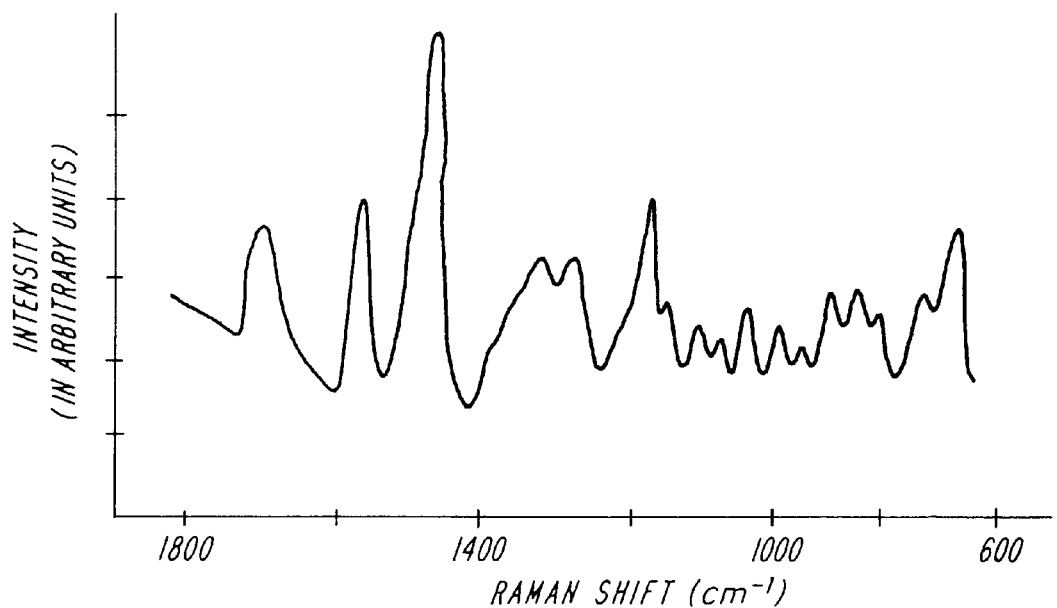
FIG. 5B is a graph of intensity in arbitrary units versus Raman shift wavelength for an atherosclerotic plaque.

FIG. 5B is a graph of intensity in arbitrary units versus Raman shift wavelength for a fibrous atherosclerotic plaque. It is known that plaques that are not calcified produce a different Raman spectra than those that are calcified. The graph displays spectral features from the sterol rings of free cholesterol and cholesterol esters, characteristic of lipid laden foam cells.

Figure 5C:
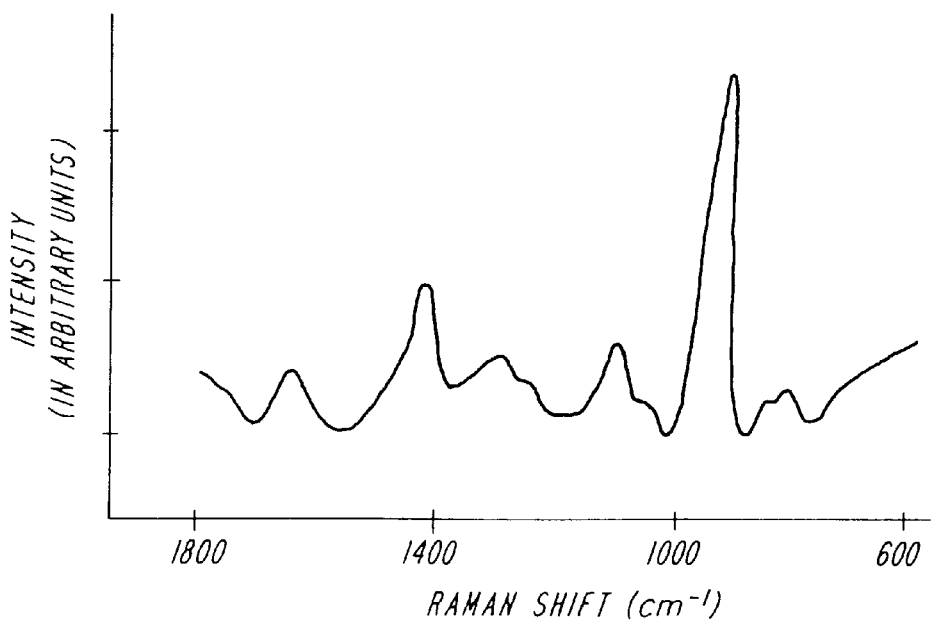
FIG. 5C is a graph of intensity in arbitrary units versus Raman shift wavelength for a calcified atherosclerotic plaque.

FIG. 5C is a graph of intensity in arbitrary units versus Raman shift wavelength for a calcified atherosclerotic plaque. The graph shows a distinguishable peak of a phosphate band at 960 $cm^{-1}$, which is characteristic of calcium salts.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for detecting the presence of a lesion in a lumen of a subject using low resolution Raman spectroscopy comprising:

a catheter comprising an excitation fiber through which multi-mode radiation can propagate to irradiate a target region of a lumen;

a multi-mode laser for irradiating the target region to produce a Raman spectrum consisting of scattered electromagnetic radiation;

a low resolution dispersion element positioned to receive and separate the scattered radiation into different wavelength components;

a detection array, optically aligned with the dispersion element for detecting at least some of the wavelength components of the scattered light; and a processor for processing data from the detector array.

2. The system of claim 1, wherein the catheter further comprises a light directing element, and the excitation fiber has a first end coupled to the multi-mode laser, and a second end coupled to the light directing element to direct the laser radiation to the target region.

3. The system of claim 1, wherein the wavelength components are separated by a resolution ranging from about 10 cm to about 100 cm.

4. The system of claim 1, wherein the system has a resolution of between 30 cm and 50 cm, wherein the resolution is determined in part by the multi-mode laser and, in part by the dispersion element.

5. The system of claim 1, wherein the multi-mode laser produces laser radiation having a wavelength of between about 700 nm and about 2.4 µm.

6. The system of claim 1, wherein the multi-mode laser produces radiation having a line width of at least 2 nm.

7. The system of claim 1, wherein the multi-mode laser has a power between about 50 mW and about 1000 mW.

8. The system of claim 1, wherein the multi-mode laser comprises a 785 nm GaAs laser diode.

9. The system of claim 1, wherein the multi-mode laser has a full-width half-maximum of 30 cm.

10. The system of claim 1, wherein the processor includes a chemometric element for applying partial least squares analysis for extracting information from said Raman spectrum.

11. The system of claim 1, wherein the dispersion element is a low resolution diffraction grating.

12. The system of claim 1, wherein the dispersion comprises a monochromator.

13. The system of claim 1, wherein the detection array comprises a diode array detector.

14. The system of claim 1, wherein the system further includes a notched filter.

15. A method for detecting the presence of a lesion in a lumen of a subject using low resolution Raman spectroscopy comprising:

providing a catheter comprising an excitation fiber through which multi-mode radiation can propagate, the excitation fiber having a first end optically coupled to a multi-mode laser, and a second end positioned in optical alignment with a light directing element to direct radiation to a site within a lumen;

inserting the catheter into the lumen;

activating the multi-mode laser to irradiate the lumen to produce a Raman spectrum consisting of scattered electromagnetic radiation;

collecting a portion of the scattered radiation;

separating the collected radiation into different wavelength components using a low resolution dispersion element;

detecting at least some of the wavelength components of the scattered light using a detection array; and processing the data from the detection array to detect the presence of a lesion.

16. The method of claim 15, further comprises identifying the components of the lesion from the data.

17. The method of claim 15, wherein the step of inserting a catheter into a lumen comprises inserting the catheter into a blood vessel.

18. The method of claim 15, wherein the step of detecting a lesion comprises detecting an atherosclerotic plaque.

19. The method of claim 16, wherein the step of identifying the components of a lesion comprises identifying components selected from the group consisting of cholesterol esters, calcium salts, free cholesterol, phospholipids and triglycerides.

20. The method of claim 15, wherein the step of processing further comprises applying a partial least squares analysis to extract chemometric information from the data.

21. The method of claim 15, wherein the step of separating and collecting the radiation comprises having a resolution of between 30 cm and 50 cm, wherein the resolution is determined in part by the multi-mode laser and, in part by the dispersion element.

\* \* \* \* \*